US008039223B2

(12) United States Patent
Ebinuma et al.

(10) Patent No.: US 8,039,223 B2
(45) Date of Patent: Oct. 18, 2011

(54) METHOD OF SELECTIVELY ASSAYING ADIPONECTIN MULTIMERS

(75) Inventors: Hiroyuki Ebinuma, Ryugasaki (JP); Hirokazu Yago, Ryugasaki (JP); Yuka Akimoto, Ryugasaki (JP); Osamu Miyazaki, Ibaraki (JP); Takashi Kadowaki, Tokyo (JP); Toshimasa Yamauchi, Tokyo (JP); Kazuo Hara, Tokyo (JP)

(73) Assignees: Sekisui Medical Co., Ltd., Tokyo (JP); Toudai TLO, Ltd., Tokyo (JP)

( * ) Notice: Subject to any disclaimer, the term of this patent is extended or adjusted under 35 U.S.C. 154(b) by 160 days.

(21) Appl. No.: 12/468,440

(22) Filed: May 19, 2009

(65) Prior Publication Data

US 2009/0291461 A1   Nov. 26, 2009

Related U.S. Application Data

(62) Division of application No. 10/575,931, filed as application No. PCT/JP2004/15260 on Oct. 15, 2004, now Pat. No. 7,608,405.

(30) Foreign Application Priority Data

Oct. 15, 2003   (JP) .................................. 2003-354930

(51) Int. Cl.
    *G01N 33/53*   (2006.01)
(52) U.S. Cl. ........ 435/7.21; 435/7.1; 436/501; 436/506; 436/518; 424/130.1; 424/178.1; 530/300; 530/350
(58) Field of Classification Search .................. None
    See application file for complete search history.

(56) References Cited

U.S. PATENT DOCUMENTS 4,444,879 A  *  4/1984  Foster et al. .................. 435/7.95

FOREIGN PATENT DOCUMENTS

| JP | 2000-304748 | 11/2000 |
| JP | 2002-363094 | 12/2002 |
| WO | 03/016906 | 2/2003 |

OTHER PUBLICATIONS

Waki et al. (The Journal of Biological Chemistry, vol. 278, No. 41, Oct. 10, 2003, pp. 40352-40363).*
Kondo et al. (Diabetes, Jul. 2002, vol. 51, No. 7, pp. 2325-2328).*
Waki, Hironori et al., "Impaired Multimerization of Human Adiponectin Mutants Associated with Diabetes", The Journal of Biological Chemistry, vol. 278, No. 41, pp. 40352-40363, 2003.
Pajvani, Utpal B. et al., "Complex Distribution, Not absolute amount of Adiponectin, Correlates with Thiazolidinedione-mediated Improvement in Insulin Sensitivity", The Journal of Biological Chemistry, vol. 279, No. 13, pp. 12152-12162, 2004.
Akamatsu, Yu "Development of "human adiponectin ELISA kit" and analysis for molecular form of serum adiponectin", Medical Science Digest, vol. 28, No. 12, pp. 502-505, 2002. ( with Partial English translation).
Yamauchi, T. et al., "The fat-derived hormone adiponectin reverses insulin resistance associated with both lipoatrophy and obesity", Nature Medicine, vol. 7 No. 8, pp. 941-946, 2001.
Nakano, Yasuko et al., "Isolation and Characterization of GBP28, a Novel Gelatin-Binding Protein Purified from Human Plasma", J. Biochem., vol. 120, No. 4, pp. 803-812, 1996.
Tsao, Tsu-Shuen et al., "Oligomerization State-dependent Activation of NF-κB Signaling Pathway by Adipocyte Complement-related Protein of 30 κDa (Acrp30)", The Journal of Biological Chemistry, vol. 277, No. 33, pp. 29359-29362, 2002.
Pajvani, Utpal B. et al, "Structure-Function Studies of the Adipocyte-secreted Hormone Acrp30/Adiponectin", The Journal of Biological Chemistry, vol. 278, No. 11, pp. 9073-9085, 2003.
Yamamoto, Yukihiro et al, "Correlation of the adipocyte-derived protein adiponectin with insulin resistance index and serum high-density lipoprotein-cholesterol, independent of body mass index, in the Japanese population", Clinical Science, vol. 103, pp. 137-142, 2002.
Tsao Tsu-Shuen, et al., "Role of Disulfide Bonds in Acrp30/Adiponectin Structure and Signaling Specificity", The Journal of Biological Chemistry by the American Society for Biochemistry and Molecular Biology, Inc. vol. 278, No. 50, Sep. 30, 2003, pp. 50810. XP-002408188.
Yukio Arita, et al. "Paradoxical Decrease of an Adipose-Specific Protein, Adiponectin, in Obesity", Biochemical and Biophysical Research Communications, XP-000867719, vol. 257, No. 1, Apr. 2, 1999, pp. 79-83.
Waki, et al. (The Journal of Biological Chemistry, vol. 278, No. 41, Oct. 10, 2003, pp. 40352-40363.

* cited by examiner

*Primary Examiner* — Lisa Cook
(74) *Attorney, Agent, or Firm* — Oblon, Spivak, McClelland, Maier & Neustadt, L.L.P.

(57) ABSTRACT

Kits and methods for selectively assaying a target adiponectin multimer in a biological sample. Such methods accurately evaluate the relationship between a disease and adiponectin through selective assay of adiponectin multimers and provide information that cannot be obtained through measurement of the total amount of adiponectin alone. A method for selectively assaying a target adiponectin multimer in a biological sample comprising distinguishing target adiponectin multimer from the other adiponectin multimers by using a protease and/or an antibody.

17 Claims, 6 Drawing Sheets

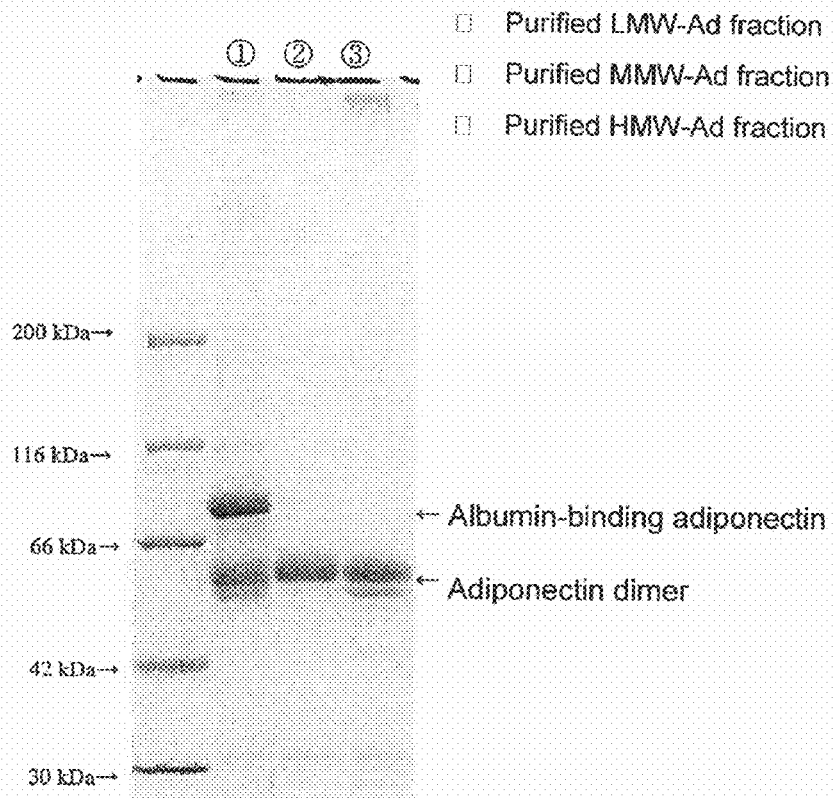
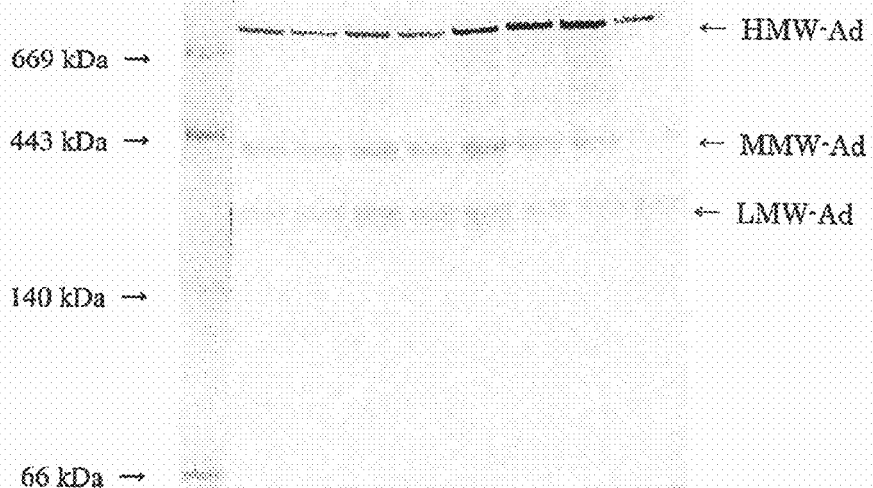

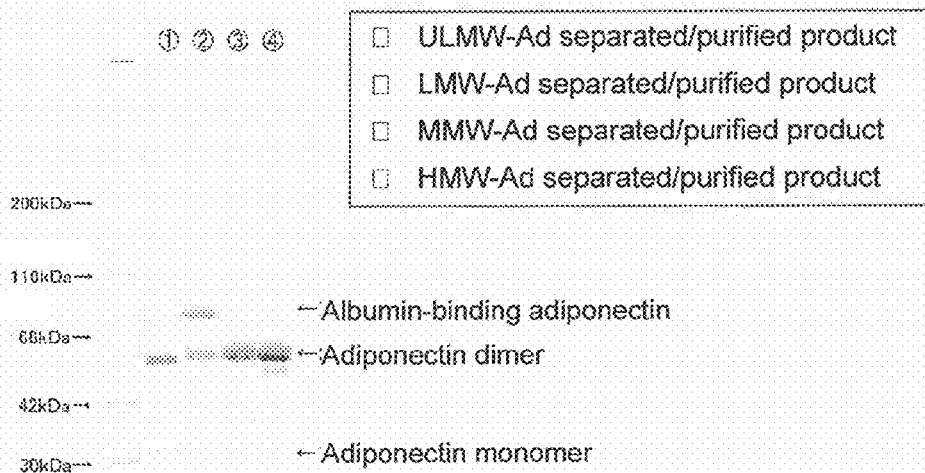
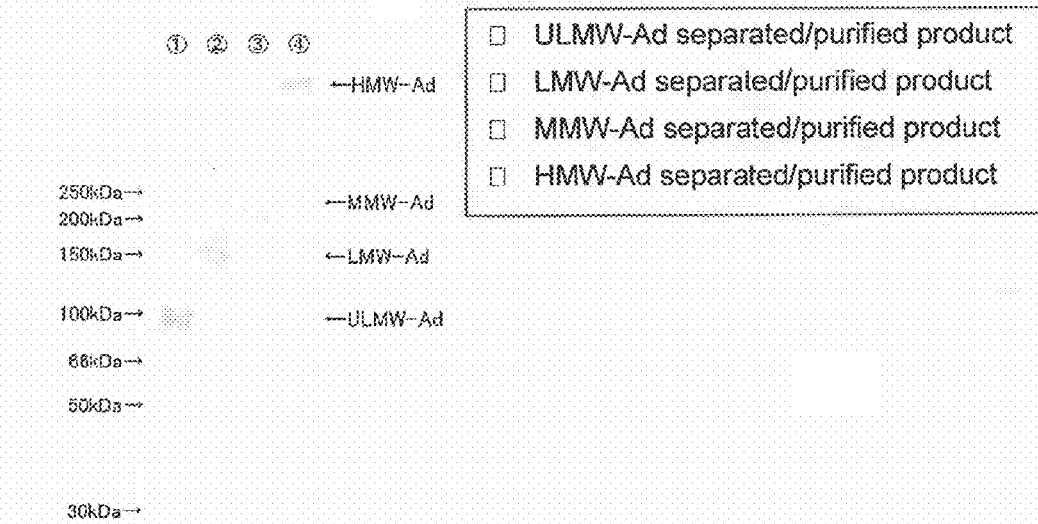

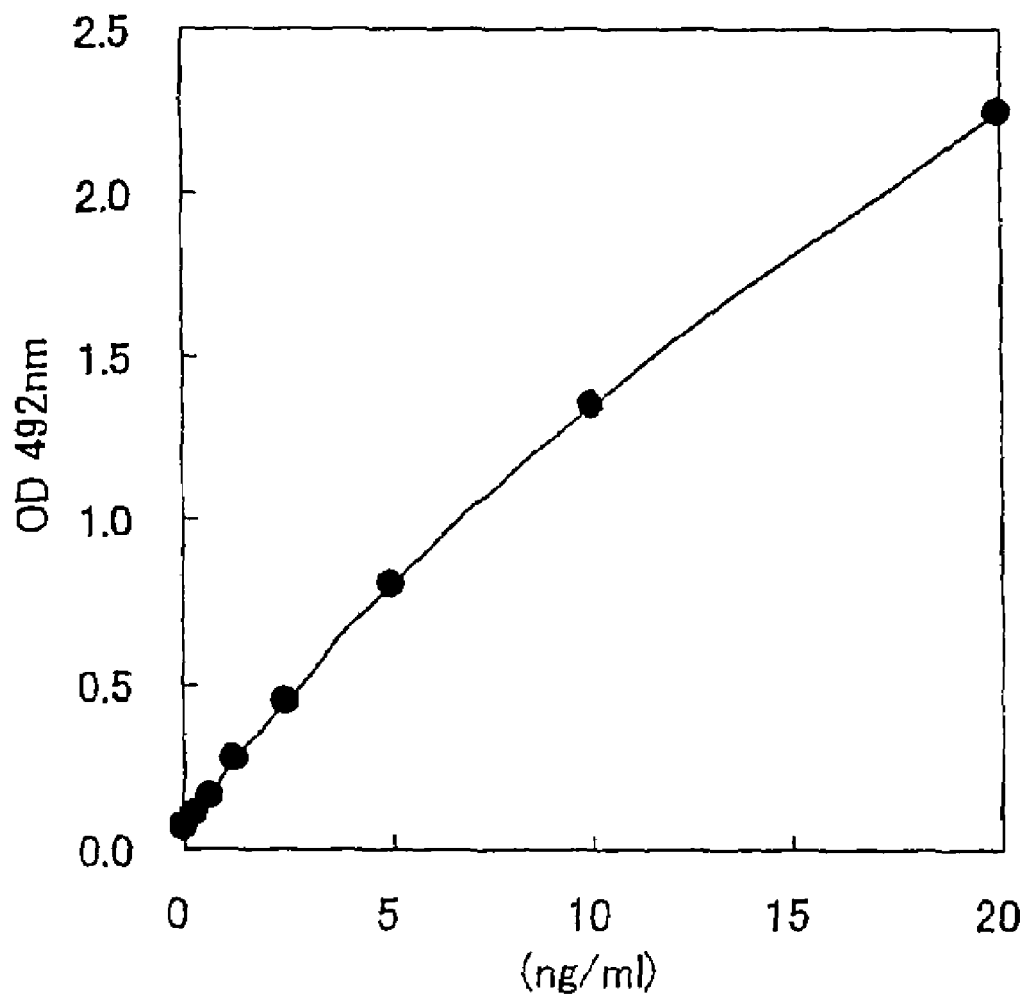

[Fig. 10]
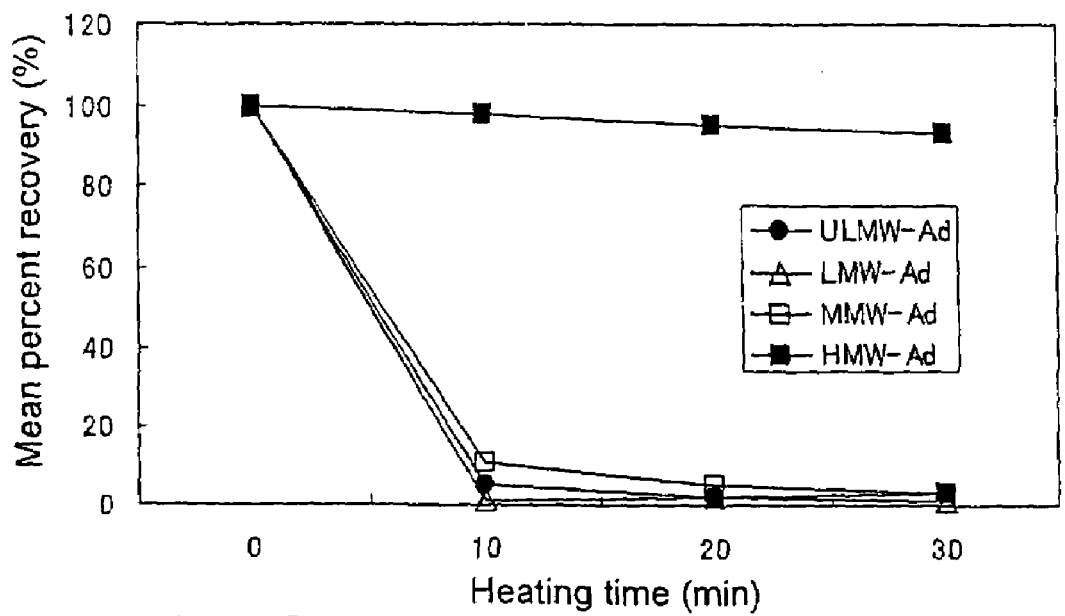
[Fig. 11]
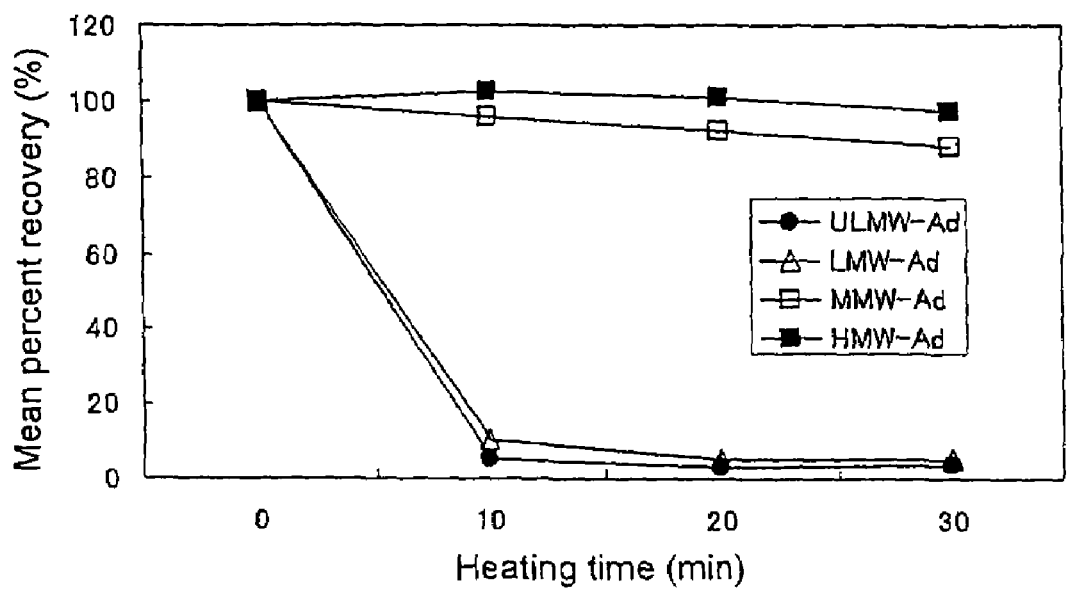

METHOD OF SELECTIVELY ASSAYING ADIPONECTIN MULTIMERS

CROSS-REFERENCE TO RELATED APPLICATIONS

This application is a division of U.S. application Ser. No. 10/575,931, filed Apr. 14, 2006 (now U.S. Pat. No. 7,608,405), which is a national-stage filing of PCT/JP04/15260, filed Oct. 15, 2004. Priority is claimed to Japan 2003-354930, filed Oct. 15, 2003.

TECHNICAL FIELD

The present invention relates to selectively assay of multimer forms of adiponectin (hereinafter referred to as adiponectin multimers) present in a biological sample.

BACKGROUND ART

Adiponectin is an insulin-sensitive hormone which is specifically secreted from fat cells, and is present in the blood at a relatively high level (5 to 10 µg/mL). A physiological effect of adiponectin has previously been reported by the present inventors; i.e., decrease in adiponectin level is a cause for type-II diabetes after obesity or a cause for sugar or lipid metabolism disorder in lipoatrophic diabetes (Non-Patent Document 1). Medical applications of adiponectin have been proposed, including diagnosis of sugar metabolism disorder; in particular, monitoring of therapeutic effect of a thiazolidine derivative which is an insulin-resistance-improving drug (Patent Document 1), and dosage of hepatic fibrogenetic suppressor utilizing effect of adiponectin, including suppression of activation and growth of stellate cells and suppression of production of extracellular matrix (Patent Document 2).

Adiponectin is classified into the C1q (Complement 1q) family on the basis of its structure, and thus has a collagen-like domain, which is a characteristic feature of the C1q family. Adiponectin has been reported to form trimer-unit-based multimers (Non-Patent Documents 2 and 3).

Relationship between the structures of adiponectin and physiological effect, activity, etc. has been reported. Tsao et al. have reported that effect of activating NF-κB is observed only in adiponectin multimers which are larger than a trimer but is not observed in a trimer and in a globular domain which lacks the collagen-like domain. Utpal et al. have reported that only high-molecular-weight adiponectin is significantly decreased through administration of insulin or glucose, and that adiponectin in which cysteine in the collagen-like domain is substituted by serine or adiponectin which has undergone a reducing treatment exhibits strong blood-sugar-reducing effect, but substantially no blood-sugar-reducing effect is observed in adiponectin which has undergone no reducing treatment and in globular adiponectin (Non-Patent Document 4).

However, adiponectin employed in these reported studies are produced through gene recombination by use of *E. coli* or the like. Therefore, behavior or action of adiponectin that is produced in an organism may not be reflected accurately. In addition, blood adiponectin level is known to differ between sexes. As compared with males, females have been reported to have significantly high blood adiponectin level (Non-Patent Document 5). A test employing mouse serum has revealed that females are high particularly in high-molecular-weight adiponectin content (Non-Patent Document 4).

As described above, through measurement of only the total amount of adiponectin, sufficient information cannot be obtained about the relationship between the structures of adiponectin and physiological effects or diseases. Therefore, there has still been demand for a method for selectively assaying adiponectin multimers present in a biological sample.

In a prior art method for assaying adiponectin, a sample to be measured is boiled in the presence of sodium dodecylsulfate (SDS) before immunoassay is performed (Patent Document 3). The boiling treatment enables exposure of an antibody-recognizing site of adiponectin which has been hidden stereostructually, in order to immunologically determine the total amount of adiponectin. Therefore, this method is not directed to selectively assay of adiponectin multimers.

A method for assaying adiponectin contained in a sample with neither SDS denaturing treatment nor thermal denaturing treatment has been disclosed (Patent Document 2, It is described in the document that native adiponectin was measured). However, no reference has been made to selectively assay, and this method cannot be employed for selectively assay.

[Patent Document 1] WO 03/016906
[Patent Document 2] JP-A-2002-363094
[Patent Document 3] JP-A-2000-304748
[Non-Patent Document 1] Yamauchi T., et al., Nat. Med., 7, 941-946, 2001
[Non-Patent Document 2] Nakano Y., et al., J. Biochem., 120, 803-812, 1996
[Non-Patent Document 3] Tsao T-S., et al., J. Biol. Chem., 277, 29359-29362, 2002
[Non-Patent Document 4] Utpal B., et al., J. Biol. Chem., 278, 9073-9085, 2003
[Non-Patent Document 5] Yamamoto Y., et al., Clin. Sci., 103, 137-142, 2002

DISCLOSURE OF THE INVENTION

Problems to be Solved by the Invention

The present invention provides a method for selectively assaying a target adiponectin multimer in a biological sample, and a method for accurately evaluating the relationship between a disease and adiponectin through selectively assay of adiponectin multimers. The selectively assay gives such information that cannot be obtained through measurement of only the total amount of adiponectin.

Means for Solving the Problem

In order to solve the problems, the present inventors have performed extensive studies and have found that the blood contains adiponectin which can be classified into the following three types on the basis of molecular weight as measured through gel filtration chromatography; 150 kDa or more and 200 kDa or less (mainly near 160 kDa) (hereinafter referred to as LMW-Ad), more than 200 kDa and less than 400 kDa (mainly near 260 kDa) (hereinafter referred to as MMW-Ad), and 400 kDa or more and 800 kDa or less (mainly near 450 kDa) (hereinafter referred to as HMW-Ad). The present inventors have performed further studies, and were eventually successful in obtaining four types of adiponectin-multimer separated and purified products from human blood. These four types can be separated through polyacrylamide (2 to 15%) electrophoresis (hereinafter may be referred to as "PAGE (2 to 15%)") under non-denaturing conditions, and are defined as ULMW-Ad, LMW-Ad, MMW-Ad, and HMW-Ad, from high mobility to low mobility. Of these four types of adiponectin, LMW-Ad, MMW-Ad, and HMW-Ad were found to correspond to the above three types of adiponectin contained in the serum. Further, the present inventors have found that LMW-Ad is an adiponectin trimer to which albumin is bound via a disulfide bond, and that, through combined use of at least an anti-adiponectin antibody and an anti-albumin antibody, LMW-Ad can be assayed selectively. Furthermore, the present inventors have found that, through molecular weight calculation with SDS-polyacrylamide (2 to 15%) electrophoresis (hereinafter may be referred to as "SDS-PAGE") after intramolecular crosslinking, ULMW-Ad is determined to be an adiponectin trimer, MMW-Ad is deduced to be a hexamer or nanomer, and HMW-Ad is deduced to be a multimer formed of monomers whose number is twice or more that of monomers forming MMW-Ad.

On the basis of these findings, the present inventors have found that, through reaction of a suitable protease with a sample containing adiponectin, adiponectin other than HMW-Ad can be digested, and that HMW-Ad that remains after digestion with the protease can be assayed selectively through use of an anti-adiponectin antibody.

The present inventors have also found that the amount of MMW-Ad contained in a sample can be determined through processing of ULMW-Ad and LMW-Ad with protease, calculation of the total amount of HMW-Ad and MMW-Ad that remain, and subtraction of the amount of HMW-Ad from the total amount of HMW-Ad and MMW-Ad, and that the amount of ULMW-Ad contained in a sample can be determined through processing of ULMW-Ad and LMW-Ad with protease, calculation of the total amount of HMW-Ad and MMW-Ad that remain, and subtraction of the total amount of HMW-Ad and MMW-Ad and the amount of LMW-Ad from the total amount of adiponectin, which has been determined selectively. The present invention has been accomplished on the basis of the findings.

Thus, the present invention provides a method for selectively assaying a target adiponectin multimer in a biological sample, comprising a step of distinguishing target adiponectin multimer from the other adiponectin multimers by using a protease and/or an antibody to assay immunologically.

The present invention also provides a method for assaying adiponectin in a biological sample, wherein the adiponectin multimer derived from human blood is of the following four types of adiponectin, and one or two of the four types of adiponectin are selected from the total adiponectin and immunoassayed, through use of a protease and/or an antibody;
(1) ULMW-Ad: exhibits the highest mobility among the four main stained bands detected when adiponectin which has been purified from human serum or human plasma is electrophoresed on polyacrylamide gel (2 to 15%) under non-denaturing conditions, and has a molecular weight around 100 kDa as measured through SDS-PAGE after intramolecular crosslinking;
(2) LMW-Ad: exhibits the second highest mobility, next to ULMW-Ad, among the four main stained bands detected when adiponectin which has been purified from human serum or human plasma is electrophoresed on polyacrylamide gel (2 to 15%) under non-denaturing conditions, has a molecular weight around 150 kDa as measured through SDS-PAGE after intramolecular crosslinking, and binds to albumin via a disulfide bond;
(3) MMW-Ad: exhibits the third highest mobility, next to LMW-Ad, among the four main stained bands detected when adiponectin which has been purified from human serum or human plasma is electrophoresed on polyacrylamide gel (2 to 15%) under non-denaturing conditions, and has a molecular weight around 250 kDa as measured through SDS-PAGE after intramolecular crosslinking; and
(4) HMW-Ad: exhibits the lowest mobility among the four main stained bands detected when adiponectin which has been purified from human serum or human plasma is electrophoresed on polyacrylamide gel (2 to 15%) under non-denaturing conditions, and has a molecular weight of 300 kDa or higher as measured through SDS-PAGE after intramolecular crosslinking.

The present invention also provides a method for evaluating a disease or a pathological condition of a human, characterized by comprising selectively assaying one or two of the above four types of adiponectin derived from the human blood from the remainder of adiponectin and immunoassaying the target adiponectin multimer(s), through use of a protease and/or an antibody, and obtaining information about the disease or the pathological condition on the basis of the results of the selectively assay.

Effects of the Invention

The present invention enables selectively assay of ULMW-Ad, LMW-Ad, MMW-Ad, and HMW-Ad, and therefore accurate evaluation of physiological effect of adiponectin and evaluation of onset, diagnosis, development, prognosis, and therapeutic effect of diseases and pathological conditions, especially type-II diabetes, arteriosclerotic disease, renal disease, hepatic disease, obesity, and metabolic syndrome.

BRIEF DESCRIPTION OF THE DRAWINGS

FIG. 3 The results of CBB-staining of LMW-Ad, MMW-Ad, and HMW-Ad after SDS-PAGE (2 to 15%), in Example 2.

FIG. 4 The analysis results of western blotting of human serum adiponectin in Example 5.

FIG. 7 The results of CBB-staining of the purified products of human-derived ULMW-Ad, LMW-Ad, MMW-Ad, and HMW-Ad, which had undergone SDS-PAGE (2 to 15%) under non-denaturing conditions, in Example 4.

FIG. 8 The results of western blotting of the purified products of human-derived ULMW-Ad, LMW-Ad, MMW-Ad, and HMW-Ad, which had undergone intramolecular crosslinking and SDS-PAGE (2 to 15%), in Example 4.

FIG. 9 The results of immunoassay of LMW-Ad (albumin-binding adiponectin) in Example 7.

FIG. 10 The results of Example 13, which shows specificity of proteinase K upon digestion of adiponectin multimers.

FIG. 11 The results of Example 13, which shows specificity of protease A "Amano" upon digestion of adiponectin multimers.

BEST MODE FOR CARRYING OUT THE INVENTION

Figure 1:
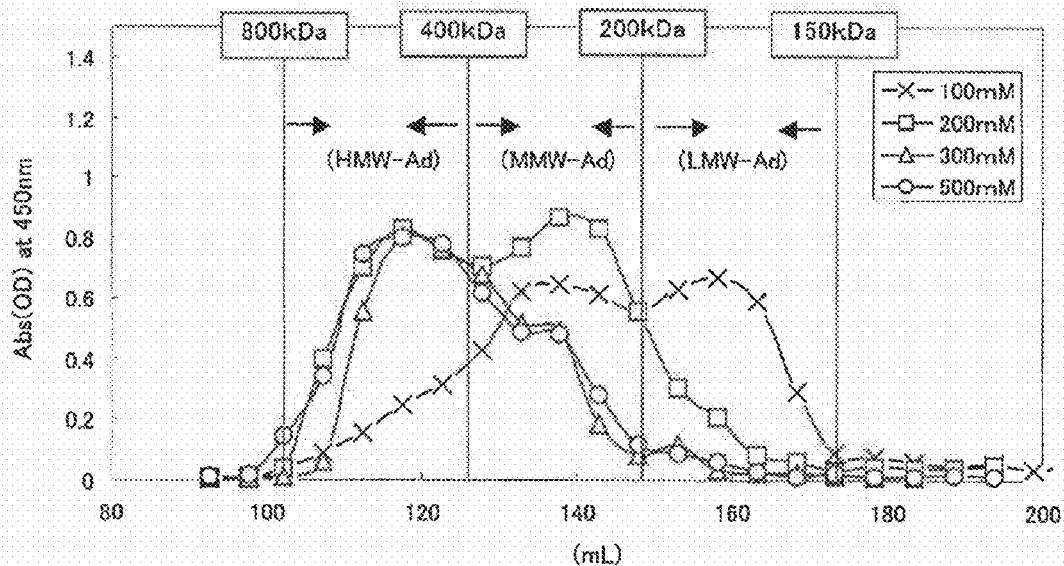
FIG. 1 Gel filtration chromatogram of adiponectin multimers in Example 1.

No particular limitation is imposed on the biological sample to be employed in the present invention, so long as the biological sample contains adiponectin multimer. Examples of the biological sample include body fluids (e.g., blood, urine), tissue extracts, and culture broth supernatants of tissue-derived cells obtained from a mammal such as a human or an animal (e.g., monkey, goat, sheep, rabbit, mouse, rat, guinea pig). In order to accurately evaluate physiological effect of adiponectin, or disease or pathological conditions of a patient, blood (serum, plasma) is preferred as a biological sample. No particular limitation is imposed on the method for obtaining a sample, so long as the method does not adversely affect adiponectin present in the sample in terms of selectively assay of adiponectin. Depending on the purposes of evaluation, a suitable method for obtaining a sample may be selected. For example, a human blood sample may be drawn from a fasting human or after administration of a drug to the human.

A method for selectively immunoassaying LMW-Ad will be described. In the method, LMW-Ad is captured and detected by use of an antibody which recognizes LMW-Ad.

Specifically, no particular limitation is imposed on the antibody employed in the method in which LMW-Ad is captured and detected by use of an antibody which recognizes LMW-Ad, so long as the antibody can recognize, capture, and detect LMW-Ad, which is a complex of adiponectin trimer and albumin. Preferred examples of the antibody include a combination of an antibody which recognizes adiponectin and an antibody which recognizes albumin, and an antibody which specifically recognizes a complex of adiponectin and albumin. A polyclonal antibody or a monoclonal antibody which recognizes adiponectin, albumin, or an adiponectin-albumin complex may be obtained through a known method through immunization of a suitable animal. Such an antibody may be commercially available. Examples of an anti-human adiponectin antibody include Goat α human Acrp30 antibody (Cosmo Bio Co., Ltd., GT), rabbit α hu adiponectin-PoAb (Cosmo Bio Co., Ltd., Chemicon), hu Acrp30-MoAb (Fujisawa Pharmaceutical Co., Ltd., BD), Mouse α hu Adiponectin MoAb (Cosmo Bio Co., Ltd., Chemicon), and anti-human ACRP30 monoclonal antibody (AX773, AX741, Ne, Na, Wako Pure Chemical Industries, Ltd.). Examples of an anti-human albumin antibody include Goat α Albumin, human antibody (Cosmo Bio Co., Ltd., BET, ACD, BMD), Mouse α Albumin, human antibody (Cosmo Bio Co., Ltd., NBT, ZYM, MED), Rabbit α Albumin, human antibody (Cosmo Bio Co., Ltd., CL, ACM), Goat α Albumin, and human antibody (Funakoshi Co., Ltd., ANT).

Specific examples of the immunoassay according to the present invention include known method such an ELISA (enzyme immunoassay), CLEIA (chemiluminescent enzyme immunoassay), RIA (radioimmunoassay), and LTIA (latex turbidimetric immunoassay). In the case of ELISA, for example, any of the following processes may be employed. Specifically, in one process, an antibody which recognizes adiponectin is immobilized to an insoluble carrier, and an enzyme-labeled antibody which recognizes albumin is used in combination with the carrier. In another process, an antibody which recognizes an adiponectin-albumin complex is immobilized to an insoluble carrier, the adiponectin-albumin complex is captured by use of the carrier, and an enzyme-labeled antibody which recognizes adiponectin or albumin is employed in combination with the carrier. Each of the assay processes will be described in detail. An antibody which recognizes adiponectin is immobilized to an insoluble carrier, and the carrier is brought into contact and mixed with a sample containing an adiponectin-albumin complex, to thereby capture the adiponectin-albumin complex onto the insoluble carrier. Subsequently, an enzyme-labeled antibody which recognizes albumin is brought into contact and mixed with the carrier, whereby a 3-component complex "insoluble carrier"-"adiponectin-albumin complex"-"enzyme-labeled antibody" is formed. Thereafter, the enzyme which labels the antibody is reacted with a suitable substrate of the enzyme, and change in absorbance attributed to the reaction product is optically measured, whereby the adiponectin-albumin complex can be qualitatively or quantitatively assayed. In the case of LTIA, an antibody which is capable of specifically binding to an adiponectin-albumin complex is carried on an insoluble carrier, and the carrier is mixed with the adiponectin-albumin complex to cause cross-linking (aggregation) of the insoluble carrier via the adiponectin-albumin complex. The resultant turbidity is optically measured, whereby the adiponectin-albumin complex can be qualitatively or quantitatively assayed. For accurate, convenient, and rapid measurement of an adiponectin-albumin complex, LTIA is preferred.

The insoluble carrier to be employed in the present invention may be an organic insoluble carrier which has been employed in routine immunoassays and which can be produced industrially on a large scale. In ELISA, a 96-well microplate made of, for example, polystyrene, which has excellent adsorbability of antibody and which is capable of maintaining biological activity stable for a long period of time, is preferred. In LTIA, polystyrene latex particles are preferred.

Various methods for carrying an antibody on such an insoluble carrier have been known, and any of the known methods may be employed in the present invention as desired. For example, an antibody may be carried (sensitized) through physical adsorption of an antibody on the surface of an insoluble carrier. Alternatively, the surface of an insoluble carrier having a functional group may be efficiently sensitized with an antibody through a known physical or chemical binding method.

No particular limitation is imposed on the reaction conditions under which an antibody-carrying insoluble carrier and/or an enzyme-labeled antibody are reacted with an adiponectin-albumin complex, so long as antigen-antibody reaction occurs under the reaction conditions. No particular limitation is imposed on the reaction mixture containing an adiponectin-albumin complex, so long as the reaction mixture does not adversely affect the antigen-antibody reaction of the adiponectin-albumin complex. For example, the reaction mixture may contain a buffer component for adjusting pH (e.g., phosphate buffer, glycine buffer, Tris buffer, Good's buffer), sodium chloride, a surfactant, or a similar substance for preventing non-specific reaction, and a stabilizer such as bovine serum albumin (BSA), sucrose, or polysaccharide polymer, as desired. The reaction mixture may also contain, in addition to the above substances which control the reactivity, water-soluble polysaccharide such as dextran, or an additive such as an enzyme inhibitor, as appropriate.

An enzyme-labeled antibody used in ELISA may be prepared through a known method. For example, through the method of Ishikawa et al. (maleimide method: "Enzyme Immunoassay, 3rd Edition," Igaku-shoin Ltd.), an untreated antibody or an antibody which has undergone limited proteolysis with a suitable protease to form $F(ab')_2$ or Fab' in accordance with needs may be labeled with an enzyme. Examples of the enzyme for labeling include peroxidase, alkaline phosphatase, β-D-galactosidase, and glucose oxidase. Enzyme activity is determined by means of a substrate, and, if needed, a color development agent. When peroxidase is employed as an enzyme, hydrogen peroxide may be employed as a substrate, and o-phenylenediamine, 3,3',5,5'-tetramethylbenzidine, 2,2'-azinodi-(3-ethylbenzthiazoline sulfonic acid) ammonium salt, or a similar substance may be employed as a color development agent. When the enzyme is alkaline phosphatase, p-nitrophenylphosphate or a similar substance may be employed as a substrate. When the enzyme is β-D-galactosidase, β-D-galactopyranoside or a similar substance may be employed as a substrate. When the enzyme is glucose oxidase, in the presence of peroxidase, β-D-glucose may be employed as a substrate of glucose oxidase, and a color development agent similar to that employed in the case of peroxidase may be employed.

When ELISA is performed, no particular limitation is imposed on the method for assaying a reaction product between a substrate and an enzyme, on the basis of enzyme activity of the enzyme-labeled antibody. For example, when the enzyme, the substrate, and the color development agent are peroxidase, hydrogen peroxide, and o-phenylenediamine, respectively, the enzyme reaction product may be detected by determining absorbance at 492 nm, which is the characteristic wavelength of the reaction product, through use of a 96-well microplate reader.

No particular limitation is imposed on the method for determining the degree of aggregation of insoluble carriers in LTIA. For example, in order to qualitatively or semi-quantatively evaluate aggregation, the degree of aggregation may be determined visually through comparison in turbidity between samples having known concentrations and the target sample. In order to quantatively evaluate aggregation, preferably, optical measurement is employed, from the viewpoint of convenience and accuracy. The optical measurement of aggregated mass may be performed through a known method. Specific examples of the optical measurement which may be employed in the present invention include so-called turbidimetric measurement (formation of aggregated mass is observed as an increase in turbidity), particle size distribution measurement (formation of aggregated mass is observed as a change in particle size distribution or mean particle size), and integrating sphere turbidimetric assay (change in forward scattered radiation caused by formation of aggregated mass is measured through use of an integrating sphere, and the ratio in intensity to transmitted radiation is compared).

A method for selectively immunoassaying HMW-Ad will now be described. A suitable protease is reacted with a sample containing adiponectin to digest adiponectin other than HMW-Ad. The HMW-Ad, which remains after digestion with protease, is assayed through use of an anti-adiponectin antibody. No particular limitation is imposed on the protease which may be employed to assay HMW-Ad selectively, so long as the protease digests adiponectin other than HMW-Ad. No particular limitation is imposed on the origin of the protease, and the protease may be derived from a microorganism, an animal, a plant, or the like. Preferably, proteinase K derived from the genus *Tritirachium* or protease derived from a microorganism belonging to, for example, the genus *Aspergillus* or *Bacillus* is employed. Examples of commercially available products of the protease derived from a microorganism belonging to the genus *Aspergillus* include protease P "Amano," protease A "Amano," and Umamizyme (products of Amano Enzyme Inc.), and sumizyme MP and sumizyme FP (products of Shin Nihon Chemical Co., Ltd.). Examples of commercially available products of the protease derived from a microorganism belonging to the genus *Bacillus* include protease N "Amano" (Amano Enzyme Inc.) and Protin PC (Daiwa Kasei K.K.). The protease may be obtained through gene recombinant technology. The protease may be chemically modified. Conditions under which processing with protease is carried out differ depending on the type of the protease employed. Preferably, the processing with protease is performed in a buffer such as phosphate buffer, Tris buffer, or Good's buffer for 5 minutes to 24 hours at 4 to 60° C. The concentration of the protease employed for processing is determined in view of specific activity of the protease, reaction temperature, reaction time, and similar factors. Typically, the protease is employed at a concentration falling within the range of 0.01 to 100 u/mL or 0.01 to 100 mg/mL.

The antibody which is used to assay HMW-Ad, which remains after processing a biological sample with protease, may be an antibody which recognizes adiponectin. An anti-adiponectin polyclonal or monoclonal antibody may be produced through immunization of a suitable animal through a known method, or may be obtained as a commercially available product. Any of these may be employed in the present invention. For example, examples of an anti-human adiponectin antibody include Goat α human Acrp30 antibody (Cosmo Bio Co., Ltd., GT), rabbit α hu adiponectin-PoAb (Cosmo Bio Co., Ltd., Chemicon), hu Acrp30-MoAb (Fujisawa Pharmaceutical Co., Ltd., BD), Mouse α hu Adiponectin MoAb (Cosmo Bio Co., Ltd., Chemicon), and anti-human ACRP30 monoclonal antibody (AX773, AX741, Ne, Na, Wako Pure Chemical Industries, Ltd.). Alternatively, a commercially available kit for determining the total adiponectin amount, such as "human adiponectin ELISA kit" (Otsuka Pharmaceutical Co., Ltd.), may be employed. An alternative method which has been developed by the present inventors (International Application which claims priority from Japanese Patent Application No. 2003-354715) may be employed, in which at least one of a reducing agent, an acid or a salt thereof, a surfactant, and a protease is added to a biological sample for reaction with adiponectin, whereby adiponectin multimers are formed into a specific form, and the resultant adiponectin is immunoassayed.

A method for selectively immunoassaying MMW-Ad will now be described. The MMW-Ad amount may be determined in the following manner; i.e., a protease which specifically digests ULMW-Ad and LMW-Ad is reacted with a sample; the total amount of the undigested MMW-Ad and HMW-Ad that remain is determined; and the amount of HMW-Ad is subtracted from the total amount. No particular limitation is imposed on the protease employed in this method, so long as the protease specifically digests only ULMW-Ad and LMW-Ad. No particular limitation is imposed on the origin of the protease, and the protease may be derived from a microorganism, an animal, a plant, or the like. A preferred protease is one derived from a microorganism belonging to, for example, the genus *Bacillus, Aspergillus*, or *Staphylococcus*. A commercially available product, including protease S "Amano" and protease A "Amano" (products of Amano Enzyme Inc.), sumizyme FP and sumizyme LP50D (products of Shin Nihon Chemical Co., Ltd.), and protease V8 (Seikagaku Corporation), may be employed. The protease may be obtained through gene recombinant technology. The protease may be chemically modified. The amount of MMW-Ad and HMW-Ad that remain may be determined through use of a commercially available kit for determining the total amount of adiponectin. The amount of HMW-Ad contained in the sample may be determined through the method described above.

The method for processing a biological sample with protease differs depending on the type of protease. Preferably, processing with protease is carried out in a buffer such as phosphate buffer, Tris buffer, or Good's buffer for 5 minutes to 24 hours at 4 to 60° C. The concentration of the protease employed for processing is determined in consideration of specific activity of the protease, reaction temperature, reaction time, and similar factors. Typically, the protease is employed at a concentration falling within the range of 0.01 to 100 u/mL or 0.01 to 100 mg/mL. The immunoassay may be performed through ELISA or LTIA with reference to the above descriptions about selectively immunoassay of LMW-Ad.

Alternatively, the MMW-Ad amount may be determined in the following manner; i.e., the total amount of ULMW-Ad, LMW-Ad, and MMW-Ad is determined as the total amount of the converted adiponectin through use of a protease described above in relation to selectively assay of HMW-Ad; and the total amount of converted ULMW-Ad and LMW-Ad, which has been determined through use of the above protease which specifically digests ULMW-Ad and LMW-Ad, is subtracted from the above total amount of ULMW-Ad, LMW-Ad, and MMW-Ad. The immunoassay may be performed through ELISA or LTIA with reference to the above descriptions about selectively immunoassay of LMW-Ad or HMW-Ad.

A method for selectively immunoassaying ULMW-Ad will now be described. The amount of ULMW-Ad may be determined through subtraction, from the total amount of adiponectin, of the total amount of LMW-Ad, MMW-Ad, and HMW-Ad determined above. Specifically, a protease which specifically digests ULMW-Ad and LMW-Ad is reacted; the total amount of MMW-Ad and HMW-Ad that remain is determined; and the total amount of MMW-Ad and HMW-Ad and the amount of LMW-Ad are subtracted from the total adiponectin amount, which has been determined separately.

According to the present invention, each of the four types of human adiponectin present in a human blood sample can be assayed selectively. Therefore, the present invention enables evaluation of onset, diagnosis, development, prognosis, and therapeutic effect of type-II diabetes, arteriosclerotic disease, renal disease, hepatic disease, obesity, and metabolic syndrome. For example, evaluation may be performed through observation of change in one or more of the amounts of ULMW-Ad, LMW-Ad, MMW-Ad, and HMW-Ad, or observation of the ratio of at least two of the total amount of adiponectin, the amount of ULMW-Ad, the amount of LMW-Ad, the amount of MMW-Ad, and the amount of HMW-Ad, and comparison of the results with a standard value. Alternatively, evaluation may be performed through observation of change in time of these amounts in the same individual. Alternatively, evaluation may be performed through correlation of a known index which has been used for a certain disease or pathological condition (for example, insulin in type-II diabetes, or HDL cholesterol in arteriosclerotic disease, or the like) with at least one of the amounts of ULMW-Ad, LMW-Ad, MMW-Ad, and HMW-Ad, or with the ratio of at least two of the amount of the total amount of adiponectin, the amount of ULMW-Ad, the amount of LMW-Ad, the amount of MMW-Ad, and the amount of HMW-Ad.

EXAMPLES

The present invention will next be described in detail by way of examples, which should not be construed as limiting the invention thereto.

<Reagents and Materials>

The reagents and materials employed in Examples and Referential Examples are;

a. antibody-binding resin wash liquid: 0.1M NaHCO$_3$—NaOH (pH 8.3) containing 0.5M NaCl;

b. antibody-binding resin eluent: 0.1M Glycine-HCl (pH 2.5);

c. antibody-binding resin neutralization liquid: 2M Tris-HCl (pH 8.0);

d. ELISA plate: 96-well microplate (product of NUNC);

e. ELISA antibody sensitization solution: PBS (pH 7.4);

f. ELISA buffer: PBS (pH 7.4) containing 1% bovine serum albumin and 0.1% Tween® 20 (Polysorbate 20);

g. Vector ABC kit (Mouse): product of Funakoshi Co., Ltd., Cat No. PK-6102;

h. DAB substrate kit (western blotting color development substrate): product of Funakoshi Co., Ltd., Cat No. SK-4100;

i. anti-human adiponectin monoclonal antibody (hu Acrp30-MoAb): product of Fujisawa Pharmaceutical Co., Ltd., BD Transduction Laboratories, product code: A12820;

j. goat anti-human adiponectin polyclonal antibody (Goat α human Acrp30 antibody): product of Cosmo Bio Co., Ltd., GT, Cat No. 421065;

k. goat anti-mouse IgG HRP-labeled antibody: Cosmo Bio Co., Ltd., product of Capple;

l. ELISA wash liquid: PBS containing 0.05% Tween®-20;

m. ELISA buffer 2: PBS containing 1% BSA and 0.05% Tween® 20;

n. goat anti-human albumin polyclonal HRP-labeled antibody (HRP-Gt anti-HSA antibody): product of PARIS; and o. HRP-Avidin: product of PIERCE.

Referential Example 1

Preparation of *E. coli* Recombinant Mouse Globular Adiponectin (rMgAd)

The globular domain sequence (corresponding to residues 104-247) of the mouse adiponectin gene sequence (NCBI accession #U37222) was inserted into BamHI and HindIII of a 6× His-tag-containing pQE30 vector, and then introduced into *E. coli*. Recombinant mouse globular adiponectin (rMgAd) expressed in *E. coli* was purified through the following process. Specifically, a soluble fraction of *E. coli* was added to Ni-NTA agarose (product of QIAGEN), and rMgAd was caused to bind for 16 hours at 4° C. rMgAd was serially eluted with imidazole, and a fraction containing adiponectin was collected and then dialyzed with PBS (pH 7.4) for three days. The protein content of the resultant rMgAd was determined by means of a Bio-Rad DC protein assay kit.

Referential Example 2

Production of Anti-rMgAd Antibody rMgAd (50 µg) prepared in Referential Example 1 and the same amount of Freund's complete adjuvant were mixed together, and two rabbits were immunized with the mixture six times, at two-week intervals, to produce antiserum. Specific antibody (IgG) present in the antiserum was purified through a routine method by use of Protein A resin (anti-rMgAd antibody).

Referential Example 3

Purification of Adiponectin Multimer (mAd) Derived from Human Blood

The anti-rMgAd antibody (500 mg) prepared in Referential Example 2 was bound to CNBr-activated Sepharose 4B (Amersham Bioscience) (50 mL), to thereby prepare anti-rMgAd antibody-binding Sepharose 4B resin. Human serum (2.5 L) was added to the anti-rMgAd antibody-binding Sepharose 4B resin, and the resin was washed thoroughly with the antibody-binding resin wash liquid. The antibody-binding resin eluent was applied to obtain a human serum adiponectin fraction (mAd), and the antibody-binding resin neutralization liquid was added to the fraction for neutralization in an amount of ⅒ that of the fraction. Thereafter, the neutralized fraction was applied to Protein A resin, and a fraction containing components which are not adsorbed to the Protein A resin was collected as purified mAd. The adiponectin content was determined by means of a "human adiponectin ELISA kit" (Otsuka Pharmaceutical Co., Ltd.).

Referential Example 4

Production of Anti-Human Adiponectin Monoclonal Antibody

The purified mAd (20 µg) obtained in Referential Example 3 was mixed with the same amount of Freund's complete adjuvant, and two mice were immunized with the mixture three or four times, at two-week intervals. The mixture was again administered to the mice three days before cell fusion. Spleen cells were collected from the immunized mice, and cell fusion was performed with P3U1 myeloma cells through a routine method by use of polyethylene glycol. Fused cells which produce anti-human adiponectin monoclonal antibody were selected through a known method. Specifically, wells that were highly reactive with mAd were selected through ELISA, and limiting dilution was performed. The selected fused cells were intraperitoneally administered to mice which had been treated with pristane, and the ascites was collected as anti-human adiponectin monoclonal antibody. Purification of the specific antibody (IgG) from the ascites was performed through a routine method by use of Protein A resin. Thus, fused cells that produce eleven anti-human adiponectin monoclonal antibody as well as such monoclonal antibodies (identification numbers 64401 to 64411) were obtained.

Example 1

Separation and Purification of Adiponectin Multimers Derived from Human Blood (1)

The purified mAd obtained in Referential Example 3 was demineralized through dialysis with 20 mM phosphate buffer (pH 7.0), adsorbed to a Gelatin-Cellulofine (Seikagaku Corporation) column, and then serially eluted with 20 mM phosphate buffers (pH 7.0) containing 0, 100, 200, 300, and 500 mM NaCl. The resultant eluate fractions, which had been obtained through use of the buffers of different NaCl concentration, contained mixtures of adiponectin of different molecular weights. Each of the eluate fractions were concentrated and then subjected to gel filtration chromatography through use of a Sephacryl S-300 (fractioned molecular weight; 10 to 1500 kDa, mean particle size; 47 µm, Amersham Bioscience). In the gel filtration chromatography, 20 mM phosphate buffer (pH 7.0) containing 150 mM NaCl was employed as the eluent. Molecular weight calibration of the Sephacryl S-300 column had been performed by use of a Gel filtration calibration Kit (Amersham Bioscience). In the chromatography, adiponectin was detected by means of a "human adiponectin ELISA kit" (Otsuka Pharmaceutical Co., Ltd.).

FIG. 1 shows the gel filtration chromatogram. The eluate fractions were divided into three portions; i.e., 150 kDa or more and 200 kDa or less (mostly near 160 kDa), more than 200 kDa and less than 400 kDa (mostly near 260 kDa), and 400 kDa or more and 800 kDa or less (mostly near 450 kDa), to thereby prepare adiponectin-multimer separated and purified products. A first product of 150 kDa or more and 200 kDa or less (mostly near 160 kDa) is referred to as LMW-Ad, a second product of more than 200 kDa and less than 400 kDa (mostly near 260 kDa) is referred to as MMW-Ad, and a third product of 400 kDa or more and 800 kDa or less (mostly near 450 kDa) is referred to as HMW-Ad.

Figure 2:
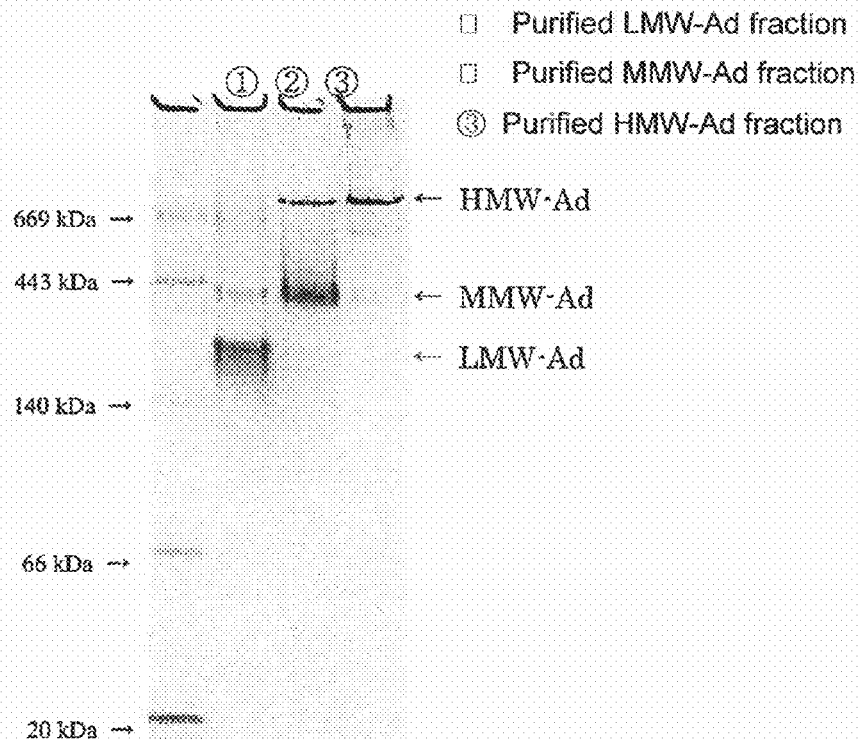
FIG. 2 The results of CBB-staining of LMW-Ad, MMW-Ad, or HMW-Ad after PAGE (2 to 15%), in Example 1.

Each of the three above-prepared adiponectin-multimer separated and purified products; i.e., LMW-Ad, MMW-Ad, and HMW-Ad was subjected to polyacrylamide gel electrophoresis (polyacrylamide concentration: 2 to 15%) (hereinafter referred to as PAGE (2 to 15%)) for separation and then to protein staining with CBB (Coomassie Brilliant Blue). FIG. 2 shows the results of the staining of the electrophoresed proteins.

In each of LMW-Ad, MMW-Ad, and HMW-Ad, bands other than the main stained band were observed but detected with considerably less clarity as compared with the main band, revealing that separation and purification were successfully completed. Since adiponectin multimers are formed based on a trimer as described above, the molecular weight of each of LMW-Ad, MMW-Ad, and HMW-Ad as measured through PAGE does not necessarily coincide with that as measured through gel filtration.

Example 2

Structure Analysis of Adiponectin Multimers (LMW-Ad, MMW-Ad, and HMW-Ad) Derived from Human Blood 1) Analysis with SDS-PAGE Each of the adiponectin-multimer separated and purified products obtained in Example 1 was subjected to SDS-PAGE (2 to 15%) under non-reducing conditions for separation and then to protein-staining with CBB. FIG. 3 shows the results of the staining of the electrophoresed proteins.

In each of LMW-Ad, MMW-Ad, and HMW-Ad, a clear stained band was observed in the vicinity of 60 kDa. The stained band was deduced to be adiponectin dimer on the basis of the reported structure and molecular weight of adiponectin. In LMW-Ad, in addition to the band near 60 kDa, a clear, unidentified stained band was observed in the vicinity of 90 kDa.

2) Analysis of the Unidentified Adiponectin Corresponding to the Band Near 90 kDa Observed in SDS-PAGE (2 to 15%)

A gel portion containing the unidentified stained band near 90 kDa, which had been detected in 1) above, was cut, and the protein was extracted by means of an electroeluter Model 422 (product of Bio-Rad Laboratories, Inc.). The extracted protein was boiled and reduced by use of a processing solution containing 2-mercaptoethanol, and the product was subjected to SDS-PAGE (2 to 15%) for separation and then transferred to a PVDF membrane, followed by protein staining with CBB. Two stained bands were observed in the vicinity of 60 kDa and 30 kDa.

Proteins showing the bands near 60 kDa and 30 kDa were analyzed in terms of N-terminus amino acid sequence. The N-terminus amino acid sequence of the protein of the band near 60 kDa was found to coincide with the N-terminus amino acid sequence of human albumin. The N-terminus amino acid sequence of the protein of the band near 30 kDa was found to coincide with a portion of the amino acid sequence of adiponectin that starts the 19th amino acid residue.

From the results described above, the protein corresponding to the band near 90 kDa, which is detected when LMW-Ad is subjected to SDS-PAGE (2 to 15%), was found to be a hetero dimer formed through disulfide-bonding of albumin monomer and adiponectin monomer. Accordingly, the adiponectin contained in the LMW-Ad fraction was found to have a structure in which adiponectin trimer and albumin are bound together via disulfide-bonding.

Example 3

Separation and Purification of Adiponectin Multimers Derived from Human Blood (2)

Purified mAd was again prepared in accordance with the method described in Referential Example 3, demineralized through dialysis with 20 mM phosphate buffer (pH 7.0), adsorbed to a Gelatin-Cellulofine column (Seikagaku Corporation), and then serially eluted with each of 20 mM phosphate buffers (pH 7.0) containing 0, 100, 200, and 500 mM NaCl. The resultant fraction eluted with 100 mM NaCl was found to contain ULMW-Ad, LMW-Ad, and MMW-Ad, and the fraction eluted with 200 mM NaCl was found to contain MMW-Ad and HMW-Ad. However, the fraction eluted with 500 mM NaCl was found to contain only HMW-Ad. Therefore, the 500 mM-NaCl eluate fraction was employed in the next step as the HMW-Ad separated and purified product. Subsequently, a Goat α human ALB antibody-binding Sepharose 4B resin was prepared in accordance with the method described in Referential Example 3 above, and the fraction eluted with 100 mM NaCl was applied to the resin, to thereby obtain a non-adsorbed fraction and an adsorbed fraction. The non-adsorbed fraction was found to contain ULMW-Ad and MMW-Ad, but the adsorbed fraction was found to contain only LMW-Ad. Therefore, the adsorbed fraction was employed in the next step as the LMW-Ad fraction. Thereafter, the non-adsorbed fraction was concentrated and then subjected to gel filtration chromatography by use of a Sephacryl S-300 (fractioned molecular weight; 10 to 1,500 kDa, mean particle size; 47 μm, Amersham Bioscience), to thereby separate ULMW-Ad and MMW-Ad from each other. The resultant fractions were employed in the next step as the ULMW-Ad separated and purified product and the MMW-Ad separated and purified product, respectively.

Separation and purification in this Example was performed based on the information obtained in separation and purification in Example 1, while the separation and purification conditions were modified. As a result, in this method, a new type of adiponectin (hereinafter referred to as ULMW-Ad) was isolated in addition to the above three types LMW-Ad, MMW-Ad, and HMW-Ad.

Figure 6:
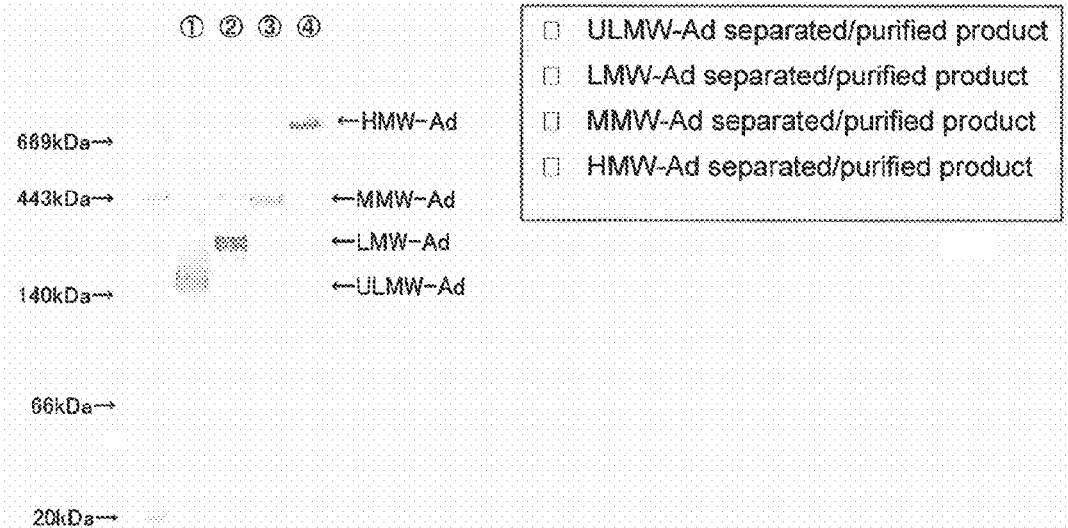
FIG. 6 The results of CBB-staining of the purified products of human-derived ULMW-Ad, LMW-Ad, MMW-Ad, and HMW-Ad after PAGE (2 to 15%), in Example 3.

The four types of adiponectin-multimer separated and purified products; i.e., ULMW-Ad, LMW-Ad, MMW-Ad, and HMW-Ad, were separated from one another through PAGE (2 to 15%) under non-denaturing conditions, followed by protein staining with CBB. FIG. 6 shows the results of the staining of the electrophoresed proteins.

Example 4

Structure Analysis of Adiponectin Multimers (ULMW-Ad, LMW-Ad, MMW-Ad, and HMW-Ad) Derived from Human Blood 1) Analysis with SDS-PAGE Each of the adiponectin-multimer separated and purified products obtained in Example 3 was subjected to SDS-PAGE (2 to 15%) under non-reducing conditions for separation and then to protein-staining with CBB. FIG. 7 shows the results of the staining of the electrophoresed proteins.

In each of ULMW-Ad, LMW-Ad, MMW-Ad, and HMW-Ad, a clear stained band was observed in the vicinity of 60 kDa. The stained band was deduced to be adiponectin dimer on the basis of the reported structure and molecular weight of adiponectin. In LMW-Ad, in addition to the band near 60 kDa, a clear, unidentified stained band was observed in the vicinity of 90 kDa. In ULMW-Ad, since a stained band attributed to monomer was observed in addition to the stained band attributed to dimer, ULMW-Ad was deduced to be a trimer. In FIG. 7, two stained bands attributed to LMW-Ad were observed. Separately, the two bands were confirmed to correspond to albumin-binding adiponectin.

2) Estimation of Molecular Weight Through Intramolecular Cross Linking

Each of the adiponectin-multimer separated and purified products obtained in Example 3 was diluted with 100 mM phosphate buffer (pH 8.0) to about 5 to about 10 μg/mL. A crosslinking agent, bis(sulfosuccinimidyl)suberate (trade name $BS^3$: product of PIERCE), was diluted with purified water to 20 mg/mL. Equal amounts of the diluted product and the diluted crosslinking agent were mixed with each other and then left to stand for 30 minutes at room temperature. Subsequently, the same amount of 100 mM Tris-HCl buffer (pH 8.0) was added to the mixture, and the resultant mixture was left to stand for 15 minutes at room temperature. The resultant liquid was subjected to SDS-PAGE (2 to 15%) under non-reducing conditions for separation, transferred to a PVDF membrane through semi-dry blotting, and then immunostained. Specifically, a transfer membrane was blocked with PBS containing 5% skim milk and 0.1% $NaN_3$, washed with PBS containing 0.1% Tween® 20, and then reacted with an anti-human adiponectin monoclonal antibody (hu Acrp30-MoAb) (1 μg/mL) for 1 hour at room temperature. The membrane was washed thoroughly with PBS containing 0.1% Tween® 20, and color was allowed to develop by use of a Vector ABC kit (Mouse) and a DAB substrate kit.

The results are shown in FIG. 8. Molecular weight calibration was performed by use of a molecular weight marker. ULMW-Ad provides a stained band near about 100 kDa and was identified to be a trimer on the basis of previously reported structure and molecular weight of adiponectin. LMW-Ad provides a stained band near about 150 kDa and was identified to be an albumin-binding trimer similar to that obtained above, on the basis of molecular weight. MMW-Ad provides a stained band near 250 kDa and was deduced to be a hexamer or a nanomer. HMW-Ad provides a stained band at a considerably high molecular weight, and was deduced to have a very high molecular weight, at least 300 kDa or higher, and to be a 12- or 18-mer or thereabouts. However, the exact form of HMW-Ad remains unidentified.

Example 5

Western Blotting Analysis of Adiponectin Contained in Human Serum

Serum samples (0.2 μL) obtained from eight healthy subjects were subjected to PAGE (2 to 15%) for separation, transferred to PVDF membrane through semi-dry blotting, and then immunostained. Specifically, a transfer membrane was blocked with PBS (pH 7.4) containing 5% skim milk and 0.1% $NaN_3$, washed with PBS (pH 7.4) containing 0.1% Tween® 20, and then reacted for 1 hour at room temperature with an anti-adiponectin monoclonal antibody (hu Acrp30-MoAb; Fujisawa Pharmaceutical Co., Ltd., BD Transduction Laboratories) (1 μg/mL). The membrane was washed thoroughly with PBS (pH 7.4) containing 0.1% Tween® 20, and color was allowed to develop by use of a Vector ABC kit (Mouse) and a DAB substrate kit (Funakoshi Co., Ltd.).

As a result, main bands were observed at similar positions as the LMW-Ad, MMW-Ad, and HMW-Ad fractions prepared in Example 1, revealing that the blood predominantly contains these three types of adiponectin (FIG. 4).

ULMW-Ad provides substantially no stained band. Although the reason for this has not yet been clarified, it is postulated that the amount of ULMW-Ad present in the blood was small (FIG. 4).

Example 6

Assay of Albumin-Binding Adiponectin (1)

Figure 5:
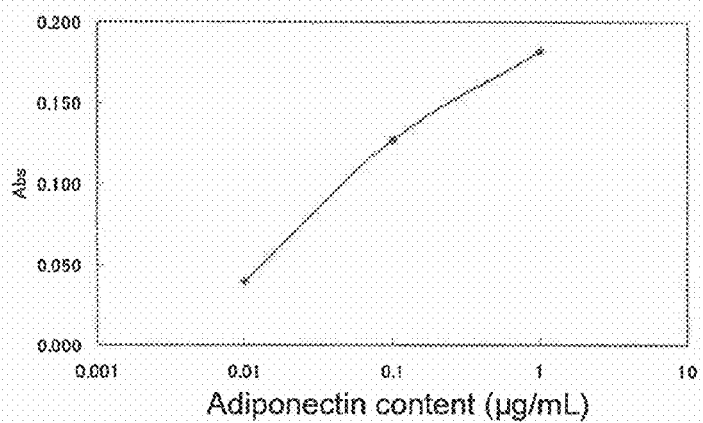
FIG. 5 The results of immunoassay of LMW-Ad (albumin-bound adiponectin) in Example 6.

A goat anti-human adiponectin polyclonal antibody (Goat α human Acrp30 antibody) was diluted with an ELISA antibody sensitization solution to 1 μg/mL, and an ELISA plate was sensitized with the diluted product. The plate was blocked with an ELISA buffer. LMW-Ad prepared in Example 1 was diluted with an ELISA buffer to 1, 0.1, and 0.01 μg/mL (Ad content) and then reacted with for 1 hour at room temperature. The plate was washed with an ELISA buffer. An anti-human albumin monoclonal antibody (Japanese Patent Application Laid-Open (kokai) No. 2001-337092) liquid which had been diluted 2,000-fold with an ELISA buffer was reacted with the ELISA plate for 1 hour at room temperature. The plate was washed with an ELISA buffer. A goat anti-mouse (Goat a mouse) IgG HRP-labeled antibody liquid which had been diluted 1,000-fold with an ELISA buffer was reacted with the plate for 1 hour at room temperature. The plate was washed with an ELISA buffer. HRP was color-developed through enzyme reaction with substrates; i.e., TMB (tetramethylbenzidine) and hydrogen peroxide. 2 N Sulfuric acid was added to the reaction mixture to stop the reaction. Absorbance at 450 nm was measured. The measurement results are shown in FIG. 5.

A concentration-dependent increase in absorbance was observed, which indicates that the sandwich immunoassay was justified. Therefore, it is confirmed that LMW-Ad is adiponectin which binds to albumin (albumin-binding adiponectin). In addition, the method of the present Example was found to enable selectively assay of LMW-Ad.

Example 7

Assay of Albumin-Binding Adiponectin (2)

(1) Linearity on Dilution

An ELISA plate was sensitized with an anti-adiponectin monoclonal antibody (64402) which had been diluted with an ELISA antibody sensitization solution to 5 μg/mL. Subsequently, the plate was blocked with an ELISA buffer containing 200 goat serum. The LMW-Ad purified product prepared in Example 3 was diluted with an ELISA buffer to 0 to 20 ng/mL (Ad content), and then reacted with the plate for 1 hour at room temperature. The plate was washed with an ELISA wash liquid, and then reacted for 1 hour at room temperature with an HRP-labeled goat anti-human albumin (HRP-Gt anti-HSA) antibody which had been diluted 1,000-fold with an ELISA buffer. The plate was washed with an ELISA wash liquid and then color-developed with an OPD color development liquid (250 mM citrate buffer containing 2 mg/mL orthophenylenediamine hydrochloride and 0.02% hydrogen peroxide, pH 5.0). A stopping liquid (1.5N sulfuric acid, 1 mM EDTA-2Na) was added to the plate to stop the reaction, and absorbance at 492 nm was measured. The assay results are shown in FIG. 9.

A concentration-dependent increase in absorbance was observed, which indicates that the sandwich immunoassay was justified. Therefore, it is confirmed that LMW-Ad is adiponectin which binds to albumin (albumin-binding adiponectin).

(2) Addition-Recovery Test

Human serum was diluted 100- to 800-fold with an ELISA buffer 2, and the LMW-Ad purified product prepared in Example 3 (0 to 50 ng/mL) was added to the diluted product. The mixture was assayed with an ELISA system similar to that of (1), and percent recovery was determined on the basis of the amount added and the amount measured. The results are shown in Table 1.

TABLE 1

| Serum dilution factor | | Amount of purified Ad added (ng/mL) | | | | |
|---|---|---|---|---|---|---|
| | | 10 | 5 | 2.5 | 1.25 | 0 |
| 100 | Calculated (ng/mL) | 13.75 | 8.75 | 6.25 | 5.00 | 3.75 |
| | Found (ng/mL) | 15.22 | 9.78 | 6.48 | 5.08 | 3.75 |
| | Recovery (%) | 111 | 112 | 104 | 102 | 100 |
| 200 | Calculated (ng/mL) | 11.97 | 6.97 | 4.47 | 3.22 | 1.97 |
| | Found (ng/mL) | 12.13 | 7.13 | 4.42 | 3.31 | 1.97 |
| | Recovery (%) | 101 | 102 | 99 | 103 | 100 |
| 400 | Calculated (ng/mL) | 11.00 | 6.00 | 3.50 | 2.25 | 1.00 |
| | Found (ng/mL) | 11.72 | 6.02 | 3.60 | 2.35 | 1.00 |
| | Recovery (%) | 106.5 | 100.4 | 102.7 | 104.6 | 100.0 |
| 800 | Calculated (ng/mL) | 10.53 | 5.53 | 3.03 | 1.78 | 0.53 |
| | Found (ng/mL) | 10.83 | 5.44 | 3.07 | 1.81 | 0.53 |
| | Recovery (%) | 103 | 98 | 101 | 102 | 100 |

In every case, a good percent recovery was obtained, revealing that the method of the present Example enables selectively assay of LMW-Ad.

Example 8

Processing with Protease (1)

The purified mAd prepared in Referential Example 3 and each commercially available protease were added to 50 mM phosphate buffer (pH 8.0), and the mixture was heated for 60 minutes at 37° C. The processing liquid was subjected to PAGE (2 to 15%) for separation and stained with CBB. Thus, the action of each protease to each of the fractions was compared with that of the control to which no protease was added (Table 2).

Through processing with protease under any of conditions 1 and 2, the fraction corresponding to LMW-Ad disappeared, while MMW-Ad and HMW-Ad remained to be present. No obvious converted product was observed. Through processing with protease under any of conditions 3 and 4, LMW-Ad was not observed, while MMW-Ad and HMW-Ad were present. In this case, a new stained band attributed to a converted product derived from LMW-Ad was observed in a low molecular weight region. Through processing with protease under any of conditions 5 and 6, LMW-Ad and MMW-Ad disappeared, whereas HMW-Ad remained to be present. In this case, a new stained band attributed to a converted product derived from LMW-Ad was observed in a low molecular weight region. The regions in which these converted products were detected through PAGE (2 to 15%) fell within the range of 30-42 kDa; the exact values may vary depending on the type of protease. These results indicate that the total amount of MMW-Ad and HMW-Ad can be determined through processing under conditions 1 or 2; the amount of only LMW-Ad or the total amount of MMW-Ad and HMW-Ad can be determined through processing under conditions 3 or 4; and the amount of only HMW-Ad or the total amount of MMW-Ad and HMW-Ad can be determined through processing under conditions 5 or 6.

phosphate buffer (pH 8.0), and the resultant mixture was heated for 30 minutes at 37° C. The processing liquid was subjected to PAGE (2 to 15%) for separation and stained with CBB. Thus, the action of each protease to each of the fractions was compared with that of the control to which no protease has been added (Table 3).

Through processing with protease under any of conditions 7 to 9, ULMW-Ad and LMW-Ad disappeared, whereas MMW-Ad and HMW-Ad remained to be present. In this case, new stained bands attributed to converted products derived from ULMW-Ad and LMW-Ad were observed in low molecular weight regions. Through processing with protease under any of conditions 10 to 12, ULMW-Ad, LMW-Ad, and MMW-Ad disappeared, and HMW-Ad remained to be present. In this case, new stained bands attributed to converted products derived from ULMW-Ad, LMW-Ad, and MMW-Ad were observed in low molecular weight regions. The regions in which these converted products were detected through PAGE (2 to 15%) fell within the range of approximately 30-40 kDa; the exact values may vary depending on the type of protease. These results indicate that the total amount of ULMW-Ad and LMW-Ad can be determined through selectively assay by use of any of the proteases employed in the processing conditions 7 to 9 and through measurement of the total amount of MMW-Ad and HMW-Ad that remain or the amount of the new Ad-converted products. In addition, the amount of HMW-Ad that remain or the total amount of ULMW-Ad, LMW-Ad, and MMW-Ad can be determined through selectively assay by use of any of the proteases employed in processing conditions 10 to 12.

TABLE 2

| | Treatment condition | | | | | |
|---|---|---|---|---|---|---|
| | 1 | 2 | 3 | 4 | 5 | 6 |
| | | | Protease | | | |
| Adiponectin multimer | Protease S "Amano" | Protease V8 | Protease A "Amano" | Sumizyme FP | Protease P "Amano" | Umamizyme |
| HMW-Ad | + | + | + | + | + | + |
| MMW-Ad | + | + | + | + | − | − |
| LMW-Ad | − | − | − | − | − | − |
| Converted product | − | − | + | + | + | + |

(−): Absent, (+): Unchanged, or production of converted product

Example 9

Processing with Protease (2)

The purified mAd analyzed in Example 3 and each commercially available protease (1 mg/mL) were added to 50 mM

TABLE 3

| | Treatment condition | | | | | |
|---|---|---|---|---|---|---|
| | 7 | 8 | 9 | 10 | 11 | 12 |
| | | | Protease | | | |
| Adiponectin multimer | Protease A "Amano" | Sumizyme FP | Sumizyme LP50D | Proteinase K | Protease P "Amano" | Protease N "Amano" |
| HMW-Ad | ++ | ++ | ++ | ++ | ++ | ++ |
| MMW-Ad | ++ | ++ | ++ | − | − | − |
| LMW-Ad | − | − | − | − | − | − |
| ULMW-Ad | − | − | − | − | − | − |
| Converted product | +++ | +++ | +++ | +++ | +++ | +++ |

(+): Decrease, (++): Unchanged, (+++): Increase, or production of converted product
(−): Absent, or no production of converted product

Example 10

Processing with Protease for Performing HMW-Ad Assay

Each of the adiponectin-multimer separated and purified products obtained in Example 3 was added to the antibody-binding resin non-adsorbing fraction obtained in Referential Example 3 (hereinafter referred to as "Ad-removed plasma") at a final concentration of 10 µg/mL or thereabouts, and the resultant mixture was employed as a sample for investigation. Proteinase K was dissolved in 50 mM Tris-HCl buffer (pH 8.0) to prepare a 5-10 u/mL solution, and the solution was employed as a pretreatment enzyme solution. The pretreatment enzyme solution (90 µL) was added to each of the samples (10 µL), and the mixture was reacted at 37° C. for predetermined periods ranging from 10 to 30 minutes. 100 mM Citrate buffer (pH 3.0, containing 2l SDS) (400 µL) was added to each of the resultant reaction mixtures to stop the enzyme reaction (pretreatment). The reaction mixture (20 µL) was diluted with an ELISA buffer 2 (1.0 mL), and the resultant mixture was employed as a pretreated sample. The amount of adiponectin that remains in the pretreated sample was determined through use of the adiponectin measurement ELISA system which will be described below.

Example 11

Processing with Protease for Measurement of the Total Amount of MMW-Ad and HMW-Ad In a manner similar to that employed in Example 10, each of the adiponectin-multimer separated and purified products obtained in Example 3 was added to an Ad-removed plasma at a final concentration of 10 µg/mL or thereabouts, and the resultant mixture was employed as a sample for investigation. Protease A "Amano" was dissolved in 50 mM Tris-HCl buffer (pH 8.0) to prepare a 0.6-11.0 mg/mL solution, and the solution was employed as a pretreatment enzyme solution. The pretreatment enzyme solution (90 µL) was added to each of the samples (10 µL), and the mixture was reacted at 37° C. for predetermined periods ranging from 10 to 30 minutes. 100 mM Citrate buffer (pH 3.0, containing 2% SDS) (400 µL) was added to each of the resultant reaction mixtures to stop the enzyme reaction (pretreatment). The reaction mixture (20 µL) was diluted with an ELISA buffer 2 (1.0 mL), and the mixture was employed as a pretreated sample. The amount of adiponectin that remains in the pretreated sample was determined through use of the adiponectin measurement ELISA system which will be described below.

Example 12

Preparation of Samples for Determining the Total Amount of Adiponectin

The present inventors have developed a method (International Application which claims priority from Japanese Patent Application No. 2003-354715), in which at least one of a reducing agent, an acid or a salt thereof, a surfactant, and a protease is added to a biological sample for reaction with adiponectin, whereby adiponectin multimers are formed into a specific form for immunoassay. In the present Example, an acid and a surfactant were employed in pretreatment. Specifically, 100 mM citrate buffer (pH 3.0, containing 2% SDS) (490 µL) was added to human plasma or human serum (10 µL), and the mixture was thoroughly stirred. The reaction mixture (20 µL) was diluted with an ELISA buffer 2 (1.0 mL), and the mixture was employed as a pretreated sample. The amount of adiponectin that remains in the pretreated sample was determined through use of the adiponectin measurement ELISA system which will be described below.

Example 13

Adiponectin Measurement ELISA System

An ELISA plate was sensitized with an anti-human adiponectin monoclonal antibody (64405) which had been diluted with PBS to 5 µg/mL. The plate was blocked with an ELISA buffer 2. Each of the pretreated samples prepared in Examples 10 and 11 was added to and reacted with the plate for 1 hour at room temperature. The plate was washed with an ELISA wash liquid. Biotin-labeled anti-human adiponectin monoclonal antibody (64404) which had been diluted 2,000-fold with an ELISA buffer 2 was reacted with the plate for 1 hour at room temperature. HRP-Avidin which had been diluted 2,000-fold with an ELISA buffer 2 was added to and reacted with the plate for 30 minutes at room temperature. The plate was washed with an ELISA wash liquid. Color was developed with an OPD color development liquid (250 mM citrate buffer containing 2 mg/mL orthophenylenediamine hydrochloride and 0.02% hydrogen peroxide, pH 5.0). A stopping solution (1.5N sulfuric acid, 1 mM EDTA-2Na) was added to the plate to stop the reaction, and absorbance at 492 nm was measured. Separately, a standard sample was prepared. Specifically, the pretreatment enzyme solution (90 µL) and 100 mM citrate buffer (pH 3.0, containing 2% SDS) (400 µL) were mixed together, and each of the samples (10 µL) was added to the mixture. The standard sample was also measured through ELISA in a manner similar to that described above, and the color development value of the standard sample was defined as 100%. The measurement value obtained from each of the samples prepared in Examples 10 and 11 was converted to %. In each case, the mean value of the thus obtained percent color development values was calculated. The results obtained from the samples prepared in Examples 10 and 11 are shown in FIGS. 10 and 11, respectively.

As is clear from the results shown in FIG. 10, through processing with protease (proteinase K), Ad multimers other than HMW-Ad contained in the plasma are digested, and assay directed specifically to HMW-Ad can be performed. The results shown in FIG. 11 indicate that, through processing with protease (protease A "Amano"), Ad multimers other than MMW-Ad and HMW-Ad contained in the plasma are digested, whereby the total amount of MMW-Ad and HMW-Ad can be determined in a manner directed specifically to MMW-Ad and HMW-Ad. The amount of MMW-Ad can be calculated through subtraction of the amount of HMW-Ad from the total amount of MMW-Ad and HMW-Ad.

As is clear from the results described above, the amount of ULMW-Ad present in a sample can be calculated in the following manner: the sample is pretreated in a manner similar to that described in Example 12, the total amount of adiponectin contained in the resultant sample is determined, the amount of LMW-Ad is determined in a manner similar to that described in Example 6 or 7, the total amount of MMW-Ad and HMW-Ad is determined in a manner similar to that described in Examples 11 and 13, and the amount of LMW-Ad and the total amount of MMW-Ad and HMW-Ad are subtracted from the total amount of adiponectin. Thus, the four types of Ad multimer present in human blood can be assayed selectively, and the total amount of these four types of adiponectin can be determined.

Example 14

Relationship with Arteriosclerotic Disease

298 Patients who suffered from type-II diabetes but had not received insulin treatment were divided into two groups; i.e., a coronary artery disease (CAD) group (90 patients having an organic lesion detected through coronary angiography (CAG)) and a non-coronary artery disease (NCAD) group (the rest, 208 patients). In a manner similar to that described above in Examples, the total adiponectin (T.Ad) content was determined, and each of the adiponectin multimers were assayed selectively. Specifically, the T.Ad content was determined through the methods described in Examples 12 and 13; the HMW-Ad content was determined through the methods described in Examples 10 and 13; and the MMW-Ad content was calculated through subtraction of the HMW-Ad content from the total amount of MMW-Ad and HMW-Ad determined through the method described in Examples 11 and 13. The total amount of ULMW-Ad and LMW-Ad was calculated through subtraction of the total amount of MMW-Ad and HMW-Ad from the T.Ad content. The obtained amounts of multimers were compared through t-test in order to determine whether or not a significant difference exists between the CAD group and the NCAD group.

The results are shown in Table 4. Between the CAD group and the NCAD group, no significant difference was observed in the T.Ad content, but a significant difference in the HMW-Ad content was observed ($p<0.05$). In the ratio (%) of the HMW-Ad content to the T.Ad content, an obvious significant difference was observed ($p<0.0001$). The results reveal that, the HMW-Ad content, especially the ratio (%) of the HMW-Ad content to the T.Ad content, can serve as a more accurate indicator of CAD than the T.Ad content.

TABLE 4

|  | CAD | | NCAD | | |
| --- | --- | --- | --- | --- | --- |
|  | Mean | Standard deviation | Mean | Standard deviation | p Value |
| Plasma T•Ad content (μg/mL) | 9.64 | 6.73 | 9.92 | 6.15 | 0.726 |
| Plasma HMW-Ad content (μg/mL) | 3.00 | 2.70 | 3.76 | 3.11 | 0.046 |
| Plasma MMW-Ad content (μg/mL) | 4.32 | 3.06 | 4.02 | 2.41 | 0.374 |
| Total of ULMW- and LMW-Ad content (μg/mL) | 2.34 | 1.92 | 2.18 | 1.60 | 0.463 |
| HMW-Ad/T•Ad in plasma (%) | 27.0 | 10.2 | 34.2 | 10.9 | <0.0001 |
| MMW-Ad/T•Ad in plasma (%) | 43.6 | 11.5 | 42.0 | 11.8 | 0.260 |

Example 15

Relationship with Metabolic Syndrome

The 298 Patients employed in Example 14 were divided into four groups on the basis of the total adiponectin content (T.Ad) and the ratio of HMW-Ad content to T.Ad content; i.e., HMW-Ad/T.Ad×100% (HMW-R), by use of the following criteria. Firstly, the mean values of T.Ad and HMW-R were calculated to be 9.8 μg/mL and 32%, respectively. Patients exhibiting T.Ad and HMW-R values which are lower than the respective mean values were classified into Group A; patients exhibiting T.Ad values which are lower than the mean value and exhibiting HMW-R values which are equal to or higher than the mean value were classified into Group B; patients exhibiting T.Ad values which are equal to or higher than the mean value and exhibiting HMW-R values which are lower than the mean value were classified into Group C; and patients exhibiting T.Ad and HMW-Ad values which are equal to or higher than the respective mean values were classified into Group D. In addition, the patients within each group were divided into two groups in view of the metabolic syndrome diagnosis criteria (JAMA, 285:2486, 2001) of the US Adult Treatment Panel III (ATPIII); i.e., a first group formed of patients exhibiting, within any two or more of the five risk factor items, risk factor levels that are higher than the respective criteria; and a second group formed of patients exhibiting, within less than two risk factor items, risk factor levels that are higher than the respective criteria. Usually, according to the diagnosis criteria of ATPIII, a patient having, in any three or more items, risk factor levels that are higher than the respective criteria is defined to suffer metabolic syndrome. However, in the present Example, a severer criterion was employed. The results are shown in Table 5.

A Kruskal-Wallis test revealed that the number of metabolic syndrome diagnosis criterion items has a statistically significant correlation with the T.Ad and HMW-R values (p value=0.001). In Groups A and C, which consist of patients exhibiting HMW-R values which are equal to or less than the mean value, the proportion of patients classified to the group exhibiting two or more metabolic syndrome diagnosis criterion items was larger. The results indicate that, as compared with the T.Ad value, the HMW-R value can serve as a good indicator for metabolic syndrome. That is, the present inventors have found for the first time that measurement of the HMW-R value and use of the HMW-R value as an index for metabolic syndrome are effective in prevention or prognosis of metabolic syndrome.

TABLE 5

|  | Less than 2 items | 2 or more items |
| --- | --- | --- |
| Group A | 44 | 92 |
| Group B | 29 | 21 |
| Group C | 6 | 13 |
| Group D | 50 | 43 |

(patients)

As is clear from the above description, even when use of the total adiponectin content as an index for a disease or pathological condition is not sufficient for evaluation of the disease or pathological condition, assay of a certain type of Ad multimers or the ratio of the amount of a certain Ad multimer fraction to the total amount of adiponectin enables prognosis and prevention of the disease or evaluation of the pathological condition.

The invention claimed is:
1. A kit comprising:
   (a) a protease which digests ULMW-Ad (ultra low molecular weight adiponectin), LMW-Ad (low molecular weight adiponectin) and MMW-Ad (middle molecular weight adiponectin) multimers; and
   (b) an anti-human adiponectin antibody which recognizes adiponectin and which is immobilized on an insoluble carrier.
2. The kit of claim 1, wherein the protease is derived from a microorganism.

3. The kit of claim 1, wherein the protease is selected from at least one of proteinase K, protease P "Amano," protease N "Amano", and Umamizyme.

4. The kit of claim 1, wherein the at least one protease includes proteinase K.

5. The kit of claim 1, wherein the anti-human adiponectin antibody is polyclonal.

6. The kit of claim 1, wherein the anti-human adiponectin antibody is monoclonal.

7. The kit of claim 1, wherein the anti-human adiponectin antibody is polyclonal.

8. The kit of claim 1, wherein the anti-human adiponectin antibody is a goat, mouse or rabbit antibody.

9. The kit of claim 1, further comprising an enzyme-labeled antibody that recognizes albumin in combination with the carrier.

10. The kit of claim 1, wherein the anti-human adiponectin antibody recognizes an adiponectin-albumin complex.

11. The kit of claim 1, which is an ELISA (enzyme linked immunosorbent assay) kit.

12. The kit of claim 1, which is a kit for CLEIA (chemiluminescent enzyme immunoassay), RIA (radioimmunoassay), or LTIA (latex turbidimetric immunoassay).

13. The kit of claim 1, further comprising at least one of a reducing agent, an acid or a salt thereof, a surfactant, a stabilizer, or a buffer.

14. The kit of claim 1, further comprising a biological sample suspected of containing adiponectin.

15. A composition comprising:
(a) a protease which digests ULMW-Ad (ultra low molecular weight adiponectin), LMW-Ad (low molecular weight adiponectin) and MMW-Ad (middle molecular weight adiponectin); and
(b) an anti-human adiponectin antibody which recognizes adiponectin and which is immobilized on an insoluble carrier.

16. The composition of claim 15, further comprising at least one of a reducing agent, an acid or a salt thereof, a surfactant, or a buffer.

17. The composition of claim 15, further comprising a biological sample suspected of containing adiponectin.

* * * * *